United States Patent [19]

Harvey et al.

[11] Patent Number: 5,192,362
[45] Date of Patent: Mar. 9, 1993

[54] DENTINE PROTECTION

[75] Inventors: Wilson Harvey, Dartford; Michael Wilson, London, both of England

[73] Assignee: National Research Development Corporation, London, England

[21] Appl. No.: 735,752

[22] PCT Filed: Feb. 10, 1989

[86] PCT No.: PCT/GB89/00134
§ 371 Date: Jun. 29, 1990
§ 102(e) Date: Jun. 29, 1990

[87] PCT Pub. No.: WO89/07437
PCT Pub. Date: Aug. 24, 1989

Related U.S. Application Data

[63] Continuation of Ser. No. 536,573, Jun. 29, 1990, abandoned.

[30] Foreign Application Priority Data

Feb. 11, 1988 [GB] United Kingdom .................. 8803157
Oct. 17, 1988 [GB] United Kingdom .................. 8824256

[51] Int. Cl.$^5$ .......................... C09K 3/00; C08L 1/00; A61C 13/02; A61C 5/00
[52] U.S. Cl. ........................................... 106/35
[58] Field of Search ...................... 106/35, 163.1, 203, 106/205, 208, 216, 213; 427/2; 433/168.1, 217.1

[56] References Cited

U.S. PATENT DOCUMENTS

| | | | |
|---|---|---|---|
| 4,315,779 | 2/1982 | Heyd et al. | 106/35 |
| 4,360,514 | 11/1982 | Buck | 424/289 |
| 4,360,515 | 11/1982 | Buck | 424/56 |
| 4,361,547 | 11/1982 | Sipos et al. | 424/56 |
| 4,362,712 | 12/1982 | Buck | 424/49 |
| 4,364,927 | 12/1982 | Sipos et al. | 424/56 |
| 4,403,089 | 9/1983 | Buck | 528/247 |
| 4,604,280 | 8/1986 | Scott | 424/49 |
| 4,775,525 | 10/1988 | Pera | 424/58 |
| 4,855,128 | 8/1989 | Lynch et al. | 424/49 |

OTHER PUBLICATIONS

Budtz-Jörgensen et al "Clinical effects of glazing denture..." Scandinavian Jour. of Dental Research, vol. 94, 1986, pp. 569-575.

*Primary Examiner*—A. Lionel Clingman
*Assistant Examiner*—William S. Parks
*Attorney, Agent, or Firm*—Nixon & Vanderhye

[57] ABSTRACT

To combat the accumulation of plaque on dentures, a non self-supporting coating of a non-toxic, negatively charged polysaccharide is applied. The polysaccharide coating is gradually sacrificed or ablated during wear. Ablation appears to remove microorganisms along with coating material. The polysaccharide is further defined by an ability to reduce the adhesion of *Streptococcus salivarius* cells in a simple in vitro bacterial adhesion test by at least 25% over a control.

9 Claims, 3 Drawing Sheets

DENTINE PROTECTION

This is a continuation of application Ser. No. 07/536,573, filed Jun. 29, 1990, now abandoned.

BACKGROUND OF THE INVENTION

1. Field of the Invention

This invention relates to the protection of dentures against the accumulation of denture plaque.

2. Description of Prior Art

It is important that denture wearers keep their dentures free from the accumulation of bacteria and their products. This is important not only from the appearance point of view (dentures having an accumulation of plaque tend to have a stained appearance) but also from the medical point of view. If dentures are not maintained adequately free from plaque material, infection may occur. This is particularly the case for the palatal-contacting surface of the denture plate since plaque accumulation frequently results in denture stomatitis, which has been estimated to affect up to 40% of denture wearers. Furthermore, accumulation of denture plaque predisposes the wearer to periodontal diseases and has been thought to give rise to infection of the dentures by Candida.

There are currently two widely used methods of removing plaque accumulation from dentures. According to the first of these, the plaque is removed chemically by use of oxidising or bleaching agents. Thus the dentures may be soaked in oxidising or bleaching agent overnight. However the use of such strong chemicals nightly over prolonged periods tends to lead to a deterioration in the dentures. Alternatively dentures are kept clean by scrubbing, generally using an abrasive agent. However again this is a cleansing method which causes deterioration in the dentures themselves.

Attempts have been made to prevent the accumulation of denture plaque within the mouth by the use of bactericidal or bacteristatic treatments in the form of rinses and mouthwashes. However the use of such bactericidal or bacteristatic formulations in the buccal cavity can lead to the selection and ultimate preponderance of resistant bacterial species which will make the formulations ineffective. The development of resistant flora is a well-known side-effect associated with the use of chemical antibacterial agents. Exposure of oral bacterial to antiseptics such as chlorhexidine can also lead to the development of resistance to these agents. In addition, the use of chemical antibacterial agents raises problems of toxicity and unwelcome side effects. In the case of chlorhexidine, for example, staining of the teeth is very common (occuring in approximately 50% of patients) and staining of the tongue has been reported. Also, using rinses and mouthwashes in this way, it is difficult to maintain an adequate concentration at the site of bacterial accumulation and thus the treatment method tends to be both wasteful and ineffective.

E. Budtz-Joergensen and S. Kaaber, Scandinavian Journal of Dental Research 94, 568–574 (1986) have suggested coating the denture with a surface glaze of a cross-linked acrylic polymer. The dentures are coated with a polyfunctional acrylic monomer mixed with a diluent and an initiator and the mixture is cured by exposure to UV light for 20 minutes. This method is claimed to reduce accumulation of plaque, but the method of coating is inconvenient and the coating cannot be renewed.

U.S. Pat. Nos. 4,360,514, 4,360,515, 4,361,547, 4,362,712, 4,364,927 and 4,403,089, assigned to Johnson & Johnson, propose the use of carboxylated or sulphonated aromatic formaldehyde condensation polymers and sulphonated alkylnaphthalenes to prevent accumulation of plague on teeth. These inventions are based on the hypothesis that these strongly anionically charged polymers deposited on the teeth repel negatively charged microorganisms responsible for generating plaque. While these patents are primarily concerned with teeth, it is mentioned that these agents can be included in denture cleansers. It is doubtful, however, whether such compounds would be approved for oral use.

It has, therefore, been a problem to find an alternative method of protecting dentures against accumulation of plaque.

Further prior art is discussed below after "Summary of the Invention", without which its context would not be apparent.

SUMMARY OF THE INVENTION

According to the present invention there is provided a method for providing dentures with a protective coating, which method comprises applying to the dentures, from an aqueous dispersion, a non self-supporting, initially adhesive but subsequently ablative (sacrificial) coating of a non-toxic negatively charge polysaccharide which, when subjected to an in vitro bacterial adhesion test, as hereinafter described, reduces the adhesion of *Streptococcus salivarius* cells to denture acrylic by at least 25%, preferably at least 50%, compared with an uncoated control. Suitable such polysaccharides include alginates, especially sodium alginates, carrageenan, gum karaya and carboxymethylcellulose, all known to be safe for oral ingestion.

The in vitro bacterial adhesion test is as follows. Strips of denture-grade acrylic sheet ($1.5 \times 6.0 \times 0.3$ cm thick) are sprayed with an aqueous dispersion of the polysaccharide and dried at room temperature, the strips are stood upright in a suspension of $10^7$ colony-forming units of *Streptococcus salivarius* per ml. of an artificial saliva obtainable by dissolving 1.492 grams of potassium chloride (KCl), 0.213 gram of calcium chloride ($CaCl_2$), 0.820 gram of sodium dihydrogen phosphate dihydrate ($NaH_2PO_4.2H_2O$) and 0.264 gram of disodium hydrogen phosphate dodecahydrate ($Na_2HPO_4.12H_2O$) in one liter of deionised water, shaken for 18 hours at 37° C. so that the saliva continually washes the coated surface, removed from the saliva, washed three times in sterile water, placed on a thin layer of mitis-salivarius agar and then immersed in said agar by pouring it over, incubated at 37° C. for 24 hours and the number of colonies of bacteria attached counted and compared with a control experiment carried out in the same way except that the acrylic strips are not coated with the polysaccharide.

The invention also includes the use of the compositions for the purposes of coating dentures as described above.

ADDITIONAL DESCRIPTION OF PRIOR ART

All these polysaccharides are well known as gelling agents or thickeners. Carrageenan is a known constituent of dentrifices (toothpastes), see e.g. U.S. Pat. No. 4,604,280 (Scott).

During the priority year, a Standard Search (RS 80965 GB) has been performed by the European Patent Office. Among the references cited were European Patent Application Publication Nos. 26332A (Richardson-Merrell) and 113079A (Richardson-Vicks). EP-26332A relates to a non-adhesive gel composition for use in improving the fit, adaptation and physical and chemical environment of dentures in the mouth. It is a demulcent (soothing) gel comprising 1-10% of a hydrophilic cellulose polymer, e.g. sodium carboxymethyl cellulose, an alginate or a xanthan gum, 5-40% of a demulcent, e.g. glycerol and 50-95% (sic) of water, all by weight. The compositions are also said to be characterised by being "antibacterial or bacteriostatic and/or mycostatic or mycocidal against *Candida albicans*, all of which can play a pathogenic role in denture stomatitis", although the specification provides no evidence of any such effects. Indeed, it says nothing about how the user is to apply the gel. It is made very clear that the gel does not stick to the dentures. Presumably the user applies it with his finger to the mouth before inserting the dentures. At all events, non-initially adhesive, demulcent compositions are of no interest in relation to the present invention.

EP-113079A relates to an adhesive for securing dentures in position in the mouth, which comprises an anhydrous mixture of karaya gum alone or in combination with sodium carboxymethylcellulose or poly(ethylene oxide) homopolymer and (b) a polyethylene glycol of defined molecular weight. Although this is supposedly an adhesive composition, it can contain up to 25 weight percent of glycerine. The present invention is not concerned with anhydrous compositions or the securing of dentures. The dentures are coated from an aqueous suspension.

The coating of the invention is to be distinguished from denture fixative seals consisting of adhesives within a self-supporting removalbe wafer-thin carrier such as "SEABOND" (Registered Trade Mark). The coating of the invention is neither self-supporting, nor instantly removable from the denture.

BRIEF DESCRIPTION OF THE ACCOMPANYING DRAWINGS

DESCRIPTION OF THE PREFERRED EMBODIMENTS

Figure 1:
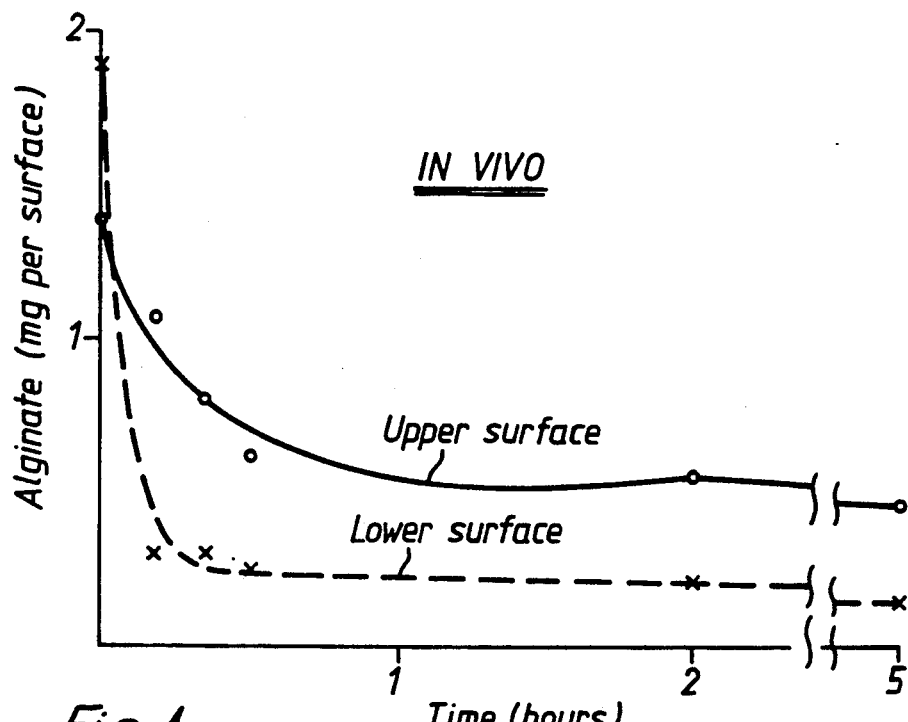
FIGS. 1 and 2 are graphs of loss of coating by ablation in vivo and in vitro respectively over 5 hours.

The coating can be applied to the dentures by any convenient method, e.g. by steeping them in or, preferably, spraying them with an aqueous dispersion (which term includes a suspension) of the polysaccharide. It is suggested that the dentures should be brushed and rinsed before the coating is applied and that they should then be left for a few minutes to allow the coating to dry. The dentures are best treated after rinsing them following removal from the mouth at night and if possible again after mid-day and evening meals.

The dentures are placed in the mouth with their protective coating. The coating, which is ablative, is gradually borne away, lost, eroded, sloughed off, sacrificed or self-removed in service and thus any undesired material which in use becomes attached will become removed with the coating. The precise degree of serviceability of the coating is conveniently determined by an in vitro ablation test which simulates the ablation of the coating during an extended period of wear such as 5 hours, representing a measure of a typical time period between the insertion of the dentures in the morning and the midday meal, between midday and evening meals and between an evening meal and removal of a dentures at night.

The in vitro ablation test is as follows. Strips of denture-grade acrylic sheet are sprayed with the polysaccharide as described above in the in vitro bacterial adhesion test. They are then stood in an artificial saliva solution as described above (but not containing any bacteria) and shaken as described above at 37° C. for 5 hours. The weight loss of the coated strips is then determined by swabbing the coating material from them and assaying it for carbohydrate by the method of Dubois et al., Analytical Chemistry 28, 350-356 (1956).

Preferably therefore, at least some of the coating, say at least 2% and usually not more than 75%, preferably not more than 50% of the original dry weight, remains after the in vitro ablation test has been carried out for 5 hours.

The polysaccharide has a net negative charge which, it is believed, acts to repel the microorganisms and the potential components of plaque and prevent such material from adhering to the dentures. While this effect may not lead to total exclusion of such material from the dentures, that which does attach will subsequently be removed as the coating itself is gradually lost during wear of the dentures. While the idea of using a negatively charged polymer is not novel, see the Johnson & Johnson patents above, the idea of providing a coating which is ablated in service is believed novel.

Inasmuch as ablation of the coating causes bacterial plaque to be removed, secondary colonisation of the plaque by *Candida spp.* would also be removed. Whereas the plaque on real teeth often contains significant amounts of calcium, denture plaque is believed to contain relatively little calcium. The invention is efficacious against such denture plaque.

The definition of the usable polysaccharides herein is formulated by an in vitro bacterial adhesion test as defined above. The test is simple to carry out in the dental laboratory. Table 1 in the Example shows results thereof. Any reduction over a control is obviously of some advantage, but a reduction of at least 25% is arbitrarily selected as conferring a reasonably good benefit. Reductions of 50% and more are achievable and a reduction of at least 75% is especially preferred.

It is also most important that the polysaccharide should be non-toxic. It will be used by the denture wearer day after day and must therefore have no short or long term adverse effect. The preferred polysaccharides, namely alginates, carrageenan and karaya gum, have been officially approved for use in foodstuffs. Other usable polysaccharides include gum arabic and carboxymethylcellulose. Alginates are conveniently produced by extraction of seaweed. They consist of a mixture of guluronic and mannuronic acids. The proportion of each will depend on the type of seaweed used in the extraction process. Alginate "DMB" contains a high proportion of guluronic acid (usually more than 60%) and forms strong gels in the presence of calcium ions. In contrast, alginate "DMF" has a lower proportion of guluronic acid (usually about 30%) and forms gels which are more elastic in the presence of calcium ions.

Many polysaccharides form a gel in water which provides a convenient form for applying the coating required according to the present invention since the dentures can simply be steeped in, or sprayed with, the gel. Conveniently, there is used a material which forms a gel in cold water.

The coating of the dentures will usually have a wet thickness of 0.5 to 3 mm.

The preferred concentration of the polysaccharide in the coating composition will depend upon the viscosity of the mixture of polymer and water and on the need to ensure an acceptable half-life for the coating. The gel needs to be sufficiently non-viscous that the denture surfaces are adequately wetted on the one hand, while sufficiently viscous to allow adequate adhesion of the coating gel to the dentures. Generally stated, a concentration of less than 3% (w/v=g/100 ml.) polymer in water is sufficient, while a concentration of at least 0.1% w/v will normally be required to provide a noticeable effect. A preferred general range is 0.5 to 2.5% w/v. A very much higher concentration than 3% can be advisable in some instances, e.g. when using gum arabic.

The coating compositions can be formulated with any non-toxic additive conducive to achieving a uniform coating on the denture, pleasant to the wearer, and having no adverse effect on denture acrylic. Examples of useful additives include anionic or non-ionic wetting agents, drying agents which will evaporate rapidly from the gel after application to the denture, colorants and flavouring agents. Where the method of application is by spraying, the compositions can also include dispersants or propellants.

Since the polysaccharides used in this invention are well known gelling or thickening agents, it is possible that they might have been suggested as vehicles for compositions for application to dentures for some other purpose, e.g. as cleansers. The present composition is not intended for cleansing dentures when they have been removed from the mouth, nor for aiding their retention in the mouth. Normally it is expected that the polysaccharide will be the principal or only active ingredient of the compositions. Certainly, since the composition is not intended as a denture cleanser, abrasive agents such as silica should not normally be included.

In this invention, the composition must adhere to the dentures upon initial application. Therefore it must not contain any component which would prevent such adhesion. For example a demulcent, such as glycerol, is undesirable unless present in a very low proportion, typically less than 5 weight percent.

The invention is further illustrated by the following Examples.

EXAMPLE 1

1. In vitro Ablation Test

Denture-grade acrylic sheet (1.5 cm×6 cm×0.3 cm thick) as used in the manufacture of dentures and obtained from the Dental Materials Department of the Eastman Dental Hospital was lightly abraded with fine emery paper to remove mould releasants and to simulate normal denture wear. The sheet was then cut into 1.5 cm×6 cm strips and the strips boiled for 15 minutes in sterile water. The sterilised strips were coated with the test compound by spraying for 5 seconds at a distance of approximately 25 cm using a standard laboratory spray gun (Jet-Pak, Scientific Supplies Ltd., London). The concentrations of polysaccharide in distilled water were chosen so as to give a viscosity of the same order, namely within the range 1500 to 6000 centipoises at 20° C. They gave a coating thickness of approximately 2 mm when wet and an estimated 30–50 μm after drying overnight at room temperature. Full details of concentration, viscosity and coating weight are shown in Table 1 below.

TABLE 1

Coating densities and viscosities of the polysaccharides used in the in vitro ablation test.

| Polysaccharide and conc. "%" = g./100 ml. | Viscosity at 20° C. centipoises | Coating density mg/cm² dry weight |
|---|---|---|
| Manucol, DMF, Kelco Co. Ltd. (2%) | 3000 | 0.26 |
| Manugel DMB (2%) | 1850 | 0.26 |
| Carboxymethyl cellulose (1%) | 4400 | 0.14 |
| Carageenan (2.5%) | 6000 | 0.60 |
| Xanthan gum (1.5%) | 2600 | 0.29 |
| Gum arabic (50%) | 1950 | 7.0 |
| Gum tragacanth (2%) | 4000 | 0.24 |
| Guar gum (1%) | 1500 | 0.18 |
| Locust bean gum (2%) | 1650 | 0.23 |
| Karaya gum (2%) | 3300 | 0.17 |

Each strip was placed in a sterile 25 ml universal container with 7.5 ml of an artificial saliva as described above. The ionic composition of the saliva is approximately $K^+$ (20 mM), $Na^+$ (6 mM), $Ca^{2+}$ (1.5 mM), $PO_4^{3-}$ (6 mM), $Cl^-$ (14 mM) and $H^+$ to pH 6.0.

The containers were placed horizontally on an orbital shaker at 37° C. and agitated at 30 cycles per minute so that the fluid was continually washing over the coated surface of the strips. 5 strips were removed at each of the following time points: 0, 2.5, 5, 15, 120, and 300 minutes and residual coating material was removed from the surface of the acrylic strips by swabbing into 1 ml of water. Duplicate 250 μl aliquots from each of these 1 ml samples were assayed for total carbohydrate using the phenol-sulphuric acid colorimetric method of Dubois et al., Analytical Chemistry, 28: 350–356 (1956). An example of a typical in vitro decay curve is given in FIG. 2 (see Section 4). The half-life values (the time taken for 50% of the dry weight of the initial coating to be removed) were calculated from decay curves constructed from the mean values of residual compound at each time point. Results are shown in Table 2. (The last column of Table 2 relates to the above-mentioned in vitro bacterial adhesion test, described in Section 2 below, but conveniently included here). The variations in the last two columns are standard deviations.

TABLE 2

| POLYSACCHARIDE | STRUCTURAL COMPONENTS | CHARGE | Conc. of polysaccharide (g./100 ml.) | In vitro ABLATION test half-life of coating (minutes) | % coating remaining after 5 h. | In vitro test for BACTERIAL ADHESION (%)* |
|---|---|---|---|---|---|---|
| Alginate DMF | poly (guluronic) and (mannuronic) acids | negative | 2 | 5.9 | 10 ± 4 | 1.3 ± 1.2 |
| Alginate DMB | Poly (guluronic) and | negative | 2 | 4.8 | 16 ± 6 | 13.0 ± 6.7 |

TABLE 2-continued

| POLYSACCHARIDE | STRUCTURAL COMPONENTS | CHARGE | Conc. of polysaccharide (g./100 ml.) | In vitro ABLATION test half-life of coating (minutes) | In vitro ABLATION test % coating remaining after 5 h. | In vitro test for BACTERIAL ADHESION (%)* |
|---|---|---|---|---|---|---|
| Carrageenan | (mannuronic) acids anhydrogalactose and galactose (suphated) | negative | 2.5 | 6.6 | 4 ± 2 | 0.8 ± 0.1 |
| Gum karaya | galactose, rhamnose and galacturonic acid | negative | 2 | 7.9 | 18 ± 5 | 2.1 ± 0.8 |
| Carboxymethylcellulose | glucopyranose (carboxymethylated) | negative | 1 | 4.3 | 15 ± 6 | 49.0 ± 8.6 |
| Gum arabic | galactopyranose, galactose, rhamnose, arabinose, glucuronic acid | negative | 50 | 9.5 | 43 ± 9 | 33.0 ± 5.1 |
| Locust bean gum | mannopyranose and galactopyranose | neutral | 2 | 42.7 | 28 ± 8 | 178 ± 72 |
| Guar gum | mannopyranose and galactopyranose | neutral | 1 | 21.0 | 25 ± 6 | 332 ± 148 |
| Gum tragacanth | galacturonic acid, galactose, fucose, xylose and arabinose | negative | 2 | 11.5 | 6 ± 2 | 238 ± 80 |
| Xanthan gum | glucose, mannose and glucuronic acid | negative | 1.5 | 11.5 | 25 ± 9 | 800 ± 311 |

*% of bacteria remaining compared with control, control = 100%.

2. Test for Adhesion of *Streptococcus salivarius* in vitro

*Streptococcus salivarius* cells were grown in tryptone soya broth overnight at 37° C. The cells were then harvested by centrifugation and resuspended in artificial saliva, of composition as described above, at a concentration of approximately $10^7$ colony forming units/ml.

Coated acrylic strips as in Section 1 above were placed upright in the suspension obtained and agitated for 18 hours at 37° C.

The strips were then removed, washed three times in sterile water and then placed on a thin layer of mitis-salivarius agar (Difco Ltd) in a Petri dish. Then a layer of this agar was poured over the strip so that it was completely immersed. This was then incubated at 37° C. for 24 hours and the number of bacteria attached was determined by counting the numbers of colonies obtained.

Taking the control count (i.e. the count obtained using untreated acrylic sheet) as 100%, the percentage of cells remaining on the coated acrylic was calculated. The results are shown in Table 2 above.

The number of bacteria adhering to acrylic strips coated with alginate, karaya gum, carrageenan, carboxymethylcellulose and gum arabic was very much less than that of the uncoated control, and particularly low in the case of alginate, karaya gum and carrageenan.

Figure 3:
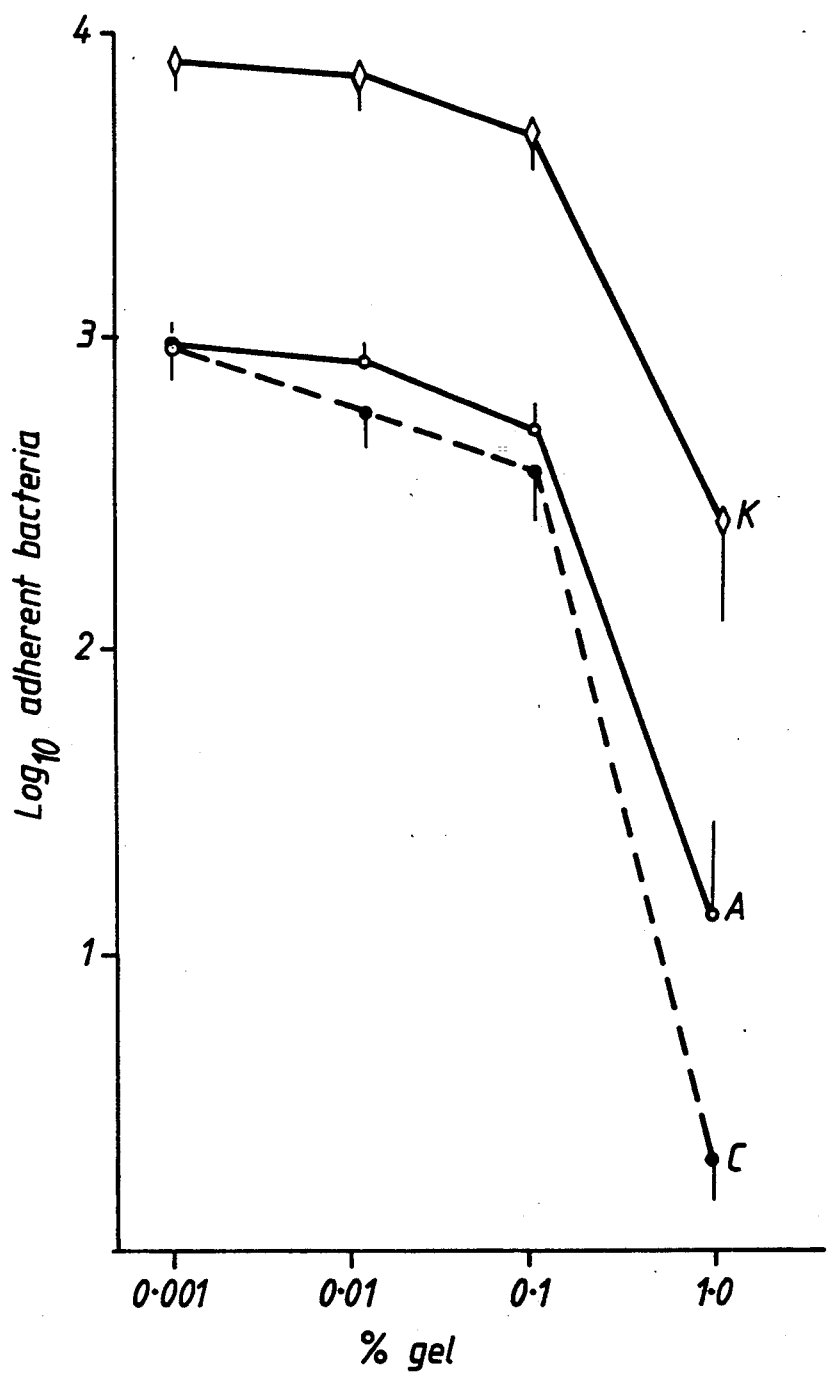
FIG. 3 is a graph of bacterial adhesion to the coated strip against concentration of the polysaccharide used for the coating.

3. Effect of Coating Material Concentration on the Adhesion of *Streptococcus salivarius* to Denture Acrylic in vitro Karaya gum, carrageenan and sodium alginate as used in Test 2 above were tested over a range of w/v concentrations (0.001%–1.0%) of the gel to determine the lowest concentration capable of inhibiting bacterial adhesion. The assays were performed as described in Section 2 above and the results are shown in the accompanying FIG. 3.

From these graphs it can be seen that, in the case of all three test compounds, the ability to inhibit adhesion decreased markedly as the concentration fell below 1%, although some effect was seen at 0.1%.

4. Correlation of an in vitro Ablation Test with an in vivo Ablation Test

An in vitro ablation test was carried out as described above using a 2% w/v dispersion of the same alginate.

An in vivo ablation test was carried out as follows. Full upper denture plates were made individually from denture acrylic for a series of volunteers. Sheets of denture-grade acrylic sheet 0.3 cm thick, as in Section 1, were lightly abraded. The upper and lower surfaces of each plate were sprayed with the test compound (as described above) and dried overnight at room temperature. The plates (5 volunteers per test) were retained in the mouth for the following time intervals on successive days: 0, 10, 20, 30, 120, and 300 minutes. On removal, the residual test compound was swabbed from the upper and lower surfaces separately into 5 ml. of distilled water. Aliquots were then assayed for total carbohydrate as described above. The half-life was determined graphically as described for the in vitro ablation test above.

Figure 2:
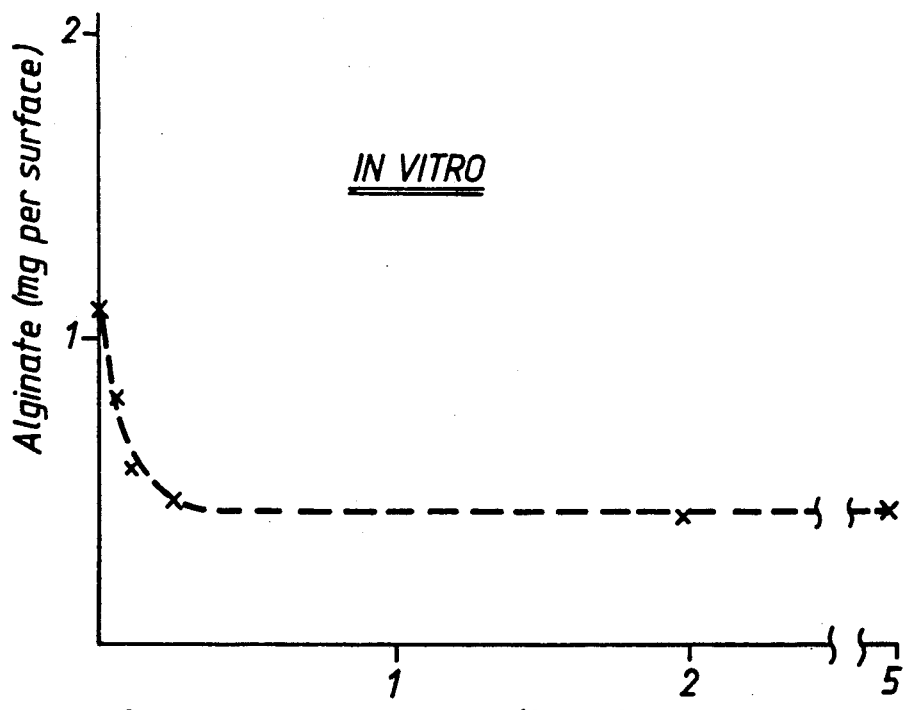

The attached FIGS. 1 and 2 illustrate the rate of loss of alginate (Manucol DMF) from upper and lower denture surfaces in vivo (FIG. 1), and from acrylic strips in vitro (FIG. 2). Referring to the in vivo test, the weights of alginate remaining after 0, 10, 20, 30, 120 and 300 minutes were: upper—1.38, 1.06, 0.8, 0.6, 0.55 and 0.45 mg; lower—1.9, 0.3, 0.3, 0.25, 0.2 and 0.13 mg respectively. It can be seen from FIG. 1 that loss of alginate from the upper surface was slower than from the lower surface. This differential was expected due to the exposed nature of the lower denture surface in the mouth. The half-life (time taken for 50% removal of the alginate coating) was 25 minutes for the upper surface and 4 minutes for the lower surface. After 5 hours, 33% of the alginate remained on the upper and 7% on the lower surface.

For the strips incubated in vitro, the weights of alginate remaining after 0, 2.5, 5, 15, 120 and 300 minutes were: 1.10, 0.81, 0.56, 0.45, 0.40 and 0.41 mg respectively. As FIG. 2 shows, there was a similar rate of alginate removal to the lower denture surface in vivo (FIG. 1), with a half-life of 5.9 minutes, and 10% remaining after 5 hours.

5. The Effects of Polysaccharide Coatings on Bacterial Adhesion to Dentures in vivo A clinical trial was carried out on the reduction of bacterial adherence to denture surfaces treated with naturally-occurring polysaccharides in accordance with the invention.

Full upper denture plates were made from denture acrylic for four volunteer subjects. The plates were worn daily for a period of five hours from 9 a.m. to 2 p.m., each day for 10 days. On alternate days the plates were coated with the test compound (in the same concentration and coating thickness as for in vitro ablation test) and allowed to dry at room temperature before insertion. On removal from the mouth after 5 hours, the plates were rinsed in 150 ml of sterile saline for 1 min. and placed in a sterile Petri dish. The upper surface (i.e. the one in contact with the palate) and the lower surface were then sampled using the swab-rinse technique described below. The plates were then cleaned ultrasonically in saline to remove any residual material before the next day's test.

Swab-rinse technique: the surface was swabbed using 2 moistened alginate wool swabs. Each swab was rolled over the surface back and forth 10 times so as to cover the whole surface area. This procedure was repeated at right angles to the first set of strokes. Both swabs were then placed in the same 10 ml of Calgon-Ringers solution (from Oxoid Ltd) and mixed in a vortex mixer to dissolve the swab, so releasing the entrapped organisms. 10-fold dilutions were then made in tryptone soya broth. Each dilution was plated in duplicate onto tryptone soya agar (containing 10% horse blood) using the Miles and Misra method, A. A. Miles and S. S. Misra, Journal of Hygiene, Cambridge, 38 732 (1938). All samples were incubated anaerobically for 48 hours, the number of colonies at each dilution counted, and hence the number of colony-forming units (cfu) per ml of the original suspension was determined. Anaerobic incubation was chosen because this consistently resulted in a much higher count than that obtained under aerobic conditions. Results are shown in Table 4 below as means of twenty determinations (5 per subject, 4 subjects per treatment). Statistical analysis by Wilcoxon's rank sum test indicated significance for the percentage reductions in adherent bacteria for the sodium, alginate and karaya gum treatments, but not for the carrageenan treatment.

TABLE 4

| Test compound | Surface | Bacteria | % Reduction |
|---|---|---|---|
| 1. Sodium Alginate (Manucol DMF; Kelco Ltd.) | lower uncoated | $8.48 \times 10^3$ | |
| | lower coated | $3.02 \times 10^3$ | 64 ($p<0.01$) |
| | upper uncoated | $8.78 \times 10^5$ | |
| | upper coated | $1.37 \times 10^5$ | 84 ($p<0.001$) |
| 2. Karaya gum (A. Bramwell Ltd.) | lower uncoated | $8.3 \times 10^3$ | |
| | lower coated | $6.3 \times 10^3$ | 24 ($p<0.05$) |
| | upper uncoated | $9.2 \times 10^5$ | |
| | upper coated | $3.3 \times 10^5$ | 64 ($p<0.001$) |
| 3. Carrageenan (A. Bramwell Ltd.) | lower uncoated | $8.76 \times 10^3$ | |
| | lower coated | $4.26 \times 10^3$ | 51 |
| | upper uncoated | $9.1 \times 10^5$ | |
| | upper coated | $4.9 \times 10^5$ | 46 |

EXAMPLE 2

Mixtures of sodium alginate solution (Manucol DMF) in water and glycerol were prepared to give final concentrations of 1% alginate (w/v) and 0, 5 and 25% glycerol (v/v). These were sprayed onto strips and dried, as described for the in vitro ablation test in our above-mentioned patent application.

Adhesion was measured by detecting the appearance of alginate in solution by ultra-violet spectrometry at 192 mm. Each strip was placed coated side-uppermost in a glass beaker containing 40 ml de-ionised, distilled water which was agitated with a magnetic stirrer. 1 ml samples were removed at 15 secs, 30 secs, 1 min, 1.5, 2, 2.5, 3, 4, 5, 6 and 7 mins and absorption measured at 192 mm (the absorbance maximum for this alginate preparation). The 1 ml sample was replaced immediately after measurement to maintain the volume of water at 40 ml. Measurements of alginate were made from triplicate strips for each concentration of glycerol.

Figure 4:
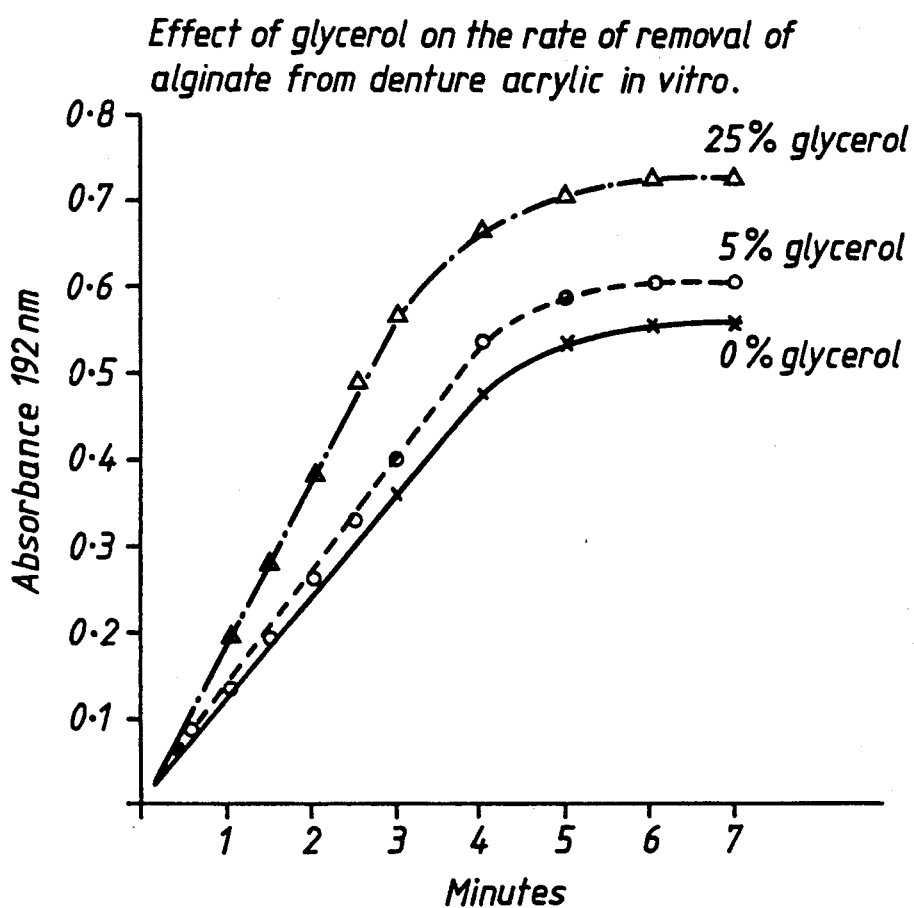
FIG. 4 is a graph showing the adverse effect of glycerol on the rate of initial loss of alginate from the coating and therefore on the initial adhesion of the coating.

FIG. 4 shows a plot of absorbance on the ordinate against time in minutes in the abscissa. The slopes of the linear part of the curves (up to 4 mins for 0% and 5% glycerol, up to 3 mins for 25% glycerol) were calculated by regression analysis and were as shown in the following Table 5:

TABLE 5

| rate of initial loss of alginate from the coating | | | |
|---|---|---|---|
| | Rate of loss (absorption units/minute) | | |
| | 0% glycerol | 5% glycerol | 25% glycerol |
| Replicate 1 | 0.080 | 0.111 | 0.195 |
| Replicate 2 | 0.103 | 0.107 | 0.172 |
| Replicate 3 | 0.097 | 0.119 | 0.170 |
| Mean: | 0.093 | 0.112 | 0.179 |

The results show that the addition of even 5% by weight of glycerol does have an adverse effect on adhesion.

We claim:

1. A method for providing dentures with a protective coating, which method comprises applying to the dentures, from a aqueous dispersion, a non self-supporting, initially adhesive but subsequently ablative, coating of a non-toxic, negatively charged polysaccharide which, when subjected to an in vitro bacterial adhesion test, as hereinafter defined, reduces the adhesion of *Streptococcus salivarius* cells to denture acrylic by at least 25% compared with an uncoated control, and wherein after a 5-hour in vitro ablation test, as hereinafter defined, at least 2% of the coating remains, said bacterial adhesion test comprising spraying strips of denture-grade acrylic sheet (1.5×6.0×0.3 cm thick) with an aqueous dispersion of said polysaccharide and drying them at room temperature, standing the strips upright in a suspension of $10^7$ colony-forming units of *Streptococcus salivarius* per ml of an artificial saliva obtainable by dissolving 1.492 grams of potassium chloride (KCl), 0.213 gram of calcium chloride ($CaCl_2$), 0.820 gram of sodium dihydrogen phosphate dihydrate ($NaH_2PO_4.2H_2O$) and 0.264 gram of disodium hydrogen phosphate dodecahydrate ($Na_2HPO_4.12H_2O$) in one liter of deionized water, shaking the strips for 18 hours at 37° C. so that the saliva continually washes the coated surface, removing the strips from the saliva, washing them three times in sterile water, placing them on a thin layer of mitis-salivarius agar, immersing them in said agar by pouring it over the strips, incubating the immersed strips at 37° C. for 24 hours, counting the number of colonies of bacteria attached and comparing them with a control test carried out in the same way except that the strips are not coated with the polysaccharide, and said in vitro ablation test being one in which strips of denture-grade acrylic sheet are sprayed with an aqueous dispersion of the polysaccharide and dried at room temperature, the strips are stood in an artificial saliva obtainable by dissolving 1.492 grams of potassium chloride (KCl), 0.213 gram of calcium chloride ($CaCl_2$), 0.820 gram of sodium dihydrogen phosphate dihydrate ($NaH_2PO_4.2H_2O$) and 0.264 gram of disodium hydrogen phosphate dodecahydrate ($Na_2HPO_4.12H_2O$) in one liter of deionized water and shaken at 37° C. for 5 hours so that the solution continually washes the coated surface, and the weight loss of the coated strips is determined by swabbing the coating material from them and assaying it for carbohydrate.

2. A method according to claim 1, wherein in the in vitro bacterial adhesion test the reduction is at least 50%.

3. A method according to claim 1, wherein in the 5-hour in vitro ablation test not more than 75% of the coating remains.

4. A method according to claim 3, wherein in the 5-hour in vitro ablation test not more than 50% of the coating remains.

5. A method according to claim 1, wherein the polysaccharide is karaya gum, carrageenan or sodium alginate.

6. A method according to claim 1, wherein the aqueous dispersion is a gel.

7. A method according to claim 6, wherein the dentures are sprayed with or steeped in the aqueous gel.

8. A method according to claim 1, wherein the aqueous dispersion contains no demulcent or less than 5 weight percent of a demulcent.

9. A method according to claim 1, wherein said coating has a viscosity in the range of about 1500 to 6000 centipoises at 20° C.

* * * * *